United States Patent
Matsuda et al.

(10) Patent No.: US 8,540,766 B2
(45) Date of Patent: Sep. 24, 2013

(54) BIOFILM FORMATION INHIBITOR AND TREATMENT DEVICE THEREOF

(75) Inventors: Takehisa Matsuda, Fukuoka (JP); Ryo Maeyama, Fukuoka (JP)

(73) Assignee: Kyushu University, National University Corporation, Fukuoka (JP)

( * ) Notice: Subject to any disclaimer, the term of this patent is extended or adjusted under 35 U.S.C. 154(b) by 646 days.

(21) Appl. No.: 11/719,819

(22) PCT Filed: Nov. 16, 2005

(86) PCT No.: PCT/JP2005/021017
§ 371 (c)(1),
(2), (4) Date: Dec. 2, 2008

(87) PCT Pub. No.: WO2006/054584
PCT Pub. Date: May 26, 2006

(65) Prior Publication Data
US 2009/0099646 A1    Apr. 16, 2009

(30) Foreign Application Priority Data
Nov. 22, 2004    (JP) .................. 2004-337604

(51) Int. Cl.
*A61F 2/06*    (2006.01)
*A61F 2/00*    (2006.01)

(52) U.S. Cl.
USPC .................. 623/1.42; 623/1.46; 424/423

(58) Field of Classification Search
USPC .............. 623/1.35, 11.11, 1.42; 604/265; 424/404; 522/163; 210/764
See application file for complete search history.

(56) References Cited

U.S. PATENT DOCUMENTS

| 5,772,640 | A | * | 6/1998 | Modak et al. | 604/265 |
| 6,117,439 | A | * | 9/2000 | Kake | 424/404 |
| 6,267,897 | B1 | * | 7/2001 | Robertson et al. | 210/764 |
| 6,887,270 | B2 | * | 5/2005 | Miller et al. | 623/11.11 |
| 2006/0241201 | A1 | * | 10/2006 | Grijpma et al. | 522/163 |

FOREIGN PATENT DOCUMENTS

| EP | 1 362 603 A2 | 11/2003 |
| JP | 2002-085549 | 3/2002 |
| JP | 2004-173770 | 6/2004 |
| JP | H11-139462 | 5/2006 |
| WO | 03/066119 | 8/2003 |
| WO | 2004/040983 | 5/2004 |
| WO | 2004/040983 A1 | 5/2004 |

OTHER PUBLICATIONS

Yoda Y. et al, Different susceptibilities of *Staphylococcus* and Gram-negative rods to epigallocatechin gallate, J Infect Chemother, 2004, pp. 55-58, vol. 10(1), Springer, Japan.

(Continued)

*Primary Examiner* — Thomas J Sweet
*Assistant Examiner* — Matthew Schall
(74) *Attorney, Agent, or Firm* — Robert C. Netter, Jr.; Dann, Dorfman, Herrell & Skillman

(57) ABSTRACT

A treatment device such as a biliary stent, capable of effectively and continuously inhibiting biofilm formation, and a biofilm formation inhibitor suitable for coating on the treatment device by killing all bacteria including *E. coli* and by suppressing the growth of these bacteria, are provided. A biofilm formation inhibitor having an effective amount of catechin for inhibiting biofilm formation and a carrier that is suitable for adhesion of said catechin to a treatment device to be placed in the living body, are provided.

10 Claims, 8 Drawing Sheets

(a) Catechin (b) Catechin gallate (c) Epicatechin (d) Epi-catechin gallate (e) Gallo catechin (f) Gallocatechin gallate (g) Epigallocatechin (h) Epigallocatechin gallate

(56) References Cited

OTHER PUBLICATIONS

Tachibana H. et al, A receptor for green tea polyphenol EGCG, Nat Struct Mol Biol, 2004, pp. 380-381, vol. 11(4), Nature Publishing Group.

Kondo K. et al, Mechanistic studies of catechins as antioxidants against radical oxidation, Arch Biochem Biophys, 1999, pp. 79-86, vol. 362, Elsevier, USA.

Shimomura H. et al, Effects of various tea-extracts and macrolide agents on bacterial adherence character, St. Marianna University School of Medicine, 1992, pp. 139-146, vol. 20, Japan.

Huber B. et al, Influence of polyphenols on bacterial biofilm formation and quorom-sensing, Journal of Biosciences, 2003, pp. 879-884, vol. 58, Verlag der Zeitschrift fur Naturforschung, German.

Matsuda T et al, Photocurable Biodegradable Liquid Copolymers, Biomacromolecules, 2004, pp. 295-305, vol. 5, American Chemical Society, USA.

Maeyama R. et al, Novel bactericidal surface, Journal of Biomedical Materials Research, 2005, pp. 146-155, vol. 75A, Wiley Periodicals, Inc., USA.

Yokiko Hara-Kudo et al, Bactericidal Action of Green Tea Extract and Damage to the membrane of *Escherichia coll* O157:H7, Biocontrol Science, 2001, vol. 6, No. 1, p. 57-61.

Yoshiko Sugita-Konishi et al, Epigallocatechin gallate and gallocatechin gallate in green tea catechins inhibit extracellular release of Vero toxin from enterohemorrhagic *Escherichia coli* O157:H7, Biochimica et Biophysica Acta, 1999, 42-50, vol. 1472.

Birgit Huber et al, Influence of Polyphenols on Bacterial Biofilm Formation and Quorum-sensing, Journal of Biosciences, 2003, 879-884, vol. 58.

Wenhong Liang, A Survey of Antibacterial Effects of Tea Polyphenol, Foreign Medical Science: Stomatology, Apr. 2004, 26-28, vol. 31.

Zong Cheng-Jiang, A method to judge the existence of implicit function, Education Collegeof Liaocheng, Shandong Liaocheng, Mar. 2000, 59-62, vol. 14.

Achim Göpferich, Polymer Bulk Erosion, Macromolecules, May 5, 1997, 2598-2604, vol. 30(9).

\* cited by examiner (a) TMC/LL/PEG1k (b) TMC/PEG200

(c) TMCTMP

* A significant difference (P<0.05)

Inhibition of Biofilm formation on catechin-loaded polymers
(Confocal laser microscope)

0 wt.%      20 wt.%

Polymer: TMC/LL/PEG1k

| EGCG (mM) | 5 | 2.5 | 1.25 | 0.63 | 0.31 | 0.16 |
|---|---|---|---|---|---|---|
| E. Coli growth | − | − | − | − | + | + |

Initial concentration of E. Coli (MIC): 0.63mM (287 μg/ml)
Minimal inhibitory concentration: 1 × 10$^7$ CFU/ml

FIG. 13

BIOFILM FORMATION INHIBITOR AND TREATMENT DEVICE THEREOF

CROSS REFERENCE TO RELATED APPLICATIONS

This application claims priority under 35 U.S.C. 119 based upon Japanese Patent Application Serial No. 2004-337604, filed on Nov. 22, 2004. The entire disclosure of the aforesaid application is incorporated herein by reference.

FIELD OF THE INVENTION

The present invention is related to a biofilm formation inhibitor and a treatment device using thereof.

BACKGROUND OF THE INVENTION

Progressive pancreatic carcinoma and cholangioma are known for their extreme difficulties in diagnosis and treatment and as so-called intractable cancers. In other words, because the pancreas and bile duct are surrounded by other organs such as the stomach, duodenum, small intestine, large intestine, liver, gall bladder, spleen, etc., it is difficult to detect cancer, and also manifestations that are characteristic to cancer are not found in the early stages. Therefore, early detection is difficult, and when it is diagnosed as a carcinoma, it is often too late to treat it.

On the other hand, there is obstructive jaundice (a symptom of the body turning yellow), which is a symptom related in some degree to these carcinomas. This is caused when the bile duct at the head of the pancreas that runs from the liver to the duodenum (that is, a pipe that drains bile created in the liver to the alimentary canal) is obstructed by a carcinoma, stopping the discharging of the bile. Generally, the first step of treating a progressive pancreatic carcinoma/bile duct cancer is to improve this obstructive jaundice.

As a means to improve this obstructive jaundice, a biliary stent is used. This biliary stent is a plastic or metal tubular (stent), that allows the bile to drain by enlarging the section of the bile duct that became narrow, by being placed into the bile duct via the duodenal papilla like an endoscope.

However, because the bile drainage of this biliary stent is exposed to the duodenum, duodenal juice flows back into the stent lumen. As a result, various kinds of Enterobacteriacae (*Escherichia coli* bacteria, etc.) present in the duodenal juice adhere to the surface of the stent lumen, where they multiply, and form so-called biofilm by producing exobacterial materials (polysaccharide) to build a complex three-dimensional structure. Once a biofilm is formed, on its surface, gallstones (calcium bilirubinate is the main component, and the enzymes produced by the bacteria and free radicals that accompany infection contribute to formation) are deposited, which in turn closes the stent lumen.

Because of this biofilm formation, the biliary stent lumen is blocked 3 months after operation. Thus it needs to be replaced with a new biliary stent. However, because the life expectancy, for example, of a pancreatic carcinoma patient, is only about 6 months, repeated operations lessen the quality of life for the patient as well as creating a large economic burden.

Moreover, a biofilm formed on a biological surface may cause infectious diseases such as chronic bronchitis and chronic osteomyelitis. Also, when a biofilm is formed on a prosthetic substrate surface, such as prosthetic heart valve, prosthetic joint, and urethral catheter, etc., sepsis may accompany it, and in the worse case may lead to death.

Currently, in order to prevent biofilm formation in biliary stents, various antibiotics (local administration, blood administration are used (Is prophylactic ciprofloxacin effective in delaying biliary stent blockage?, Gastrointest Endosc 52:175-182). However, long-term administration of antibiotics has a high probability of causing antibiotic-resistant bacteria to emerge. Thus the period of administration is at most one week. Once a biofilm is formed, it shows strong resistance to drugs. Thus currently there is no effective drug for it.

Moreover, in order to suppress bacterial adhesion to stent surfaces, biliary stents with a coating of a highly hydrophilic surface polymer (Product name: Hydromer) and stents formed by fluoropolymers (PFA; perfluoroalkoxy PTFE) which is reported to have little adhesion with animal cells, have also been developed. However, these materials cannot suppress bacterial growth. Therefore, if a small amount of bacteria with a high proliferating ability (the doubling time of the *E. coli* is 30 minutes) adheres on their surfaces, they cannot prevent the bacteria's growth, and thus they are unable to inhibit biofilm formation.

Also, in order to suppress bacterial growth, drug-eluting polymers using antibiotic and silver ion have been developed, which showed effectiveness at the experimental level. However, toxicity and effects on the living body pose problems, Thus, they have not been put to practical use for the human body.

As mentioned above, conventionally, the administering of antibiotics and the coating of a fluoropolymer have been used in order to prevent biofilm formation on the biliary stent lumen. However, neither of them is practical in terms of efficacy and safety.

SUMMARY OF THE INVENTION

The present invention was made in view of these problems, and it aims to provide a treatment device such as biliary stent capable of effectively and continuously inhibiting biofilm formation, and a biofilm formation inhibitor suitable for coating on the treatment device by killing all bacteria including *E. coli* and by suppressing the growth of these bacteria.

Furthermore, another object of the present invention is to provide a treatment device such as a biliary stent and a biofilm formation inhibitor that is suitable for coating on the treatment device, which are capable of continuously preventing biofilm formation and are safe and effective for the human body.

This invention was achieved to solve the above-mentioned problems, and according to the first aspect of the invention, a biofilm formation inhibitor having an effective amount of catechin for inhibiting biofilm formation and a carrier that is suitable for the adhesion of said catechin to a treatment device to be placed in the living body, are provided.

Catechin is a type of "polyphenol", a main constituent that gives the taste of green tea (bitterness), which is reported to possess antibacterial action (Yoda Y et al., J Infect Chemother. 2004 10(1):55-58), antitumor action (Tachibana H. et al., A receptor for green tea polyphenol EGCG. Nat Struct Mol Biol. 2004; 11(4): 380-381. Epub 2004), reactive oxygen scavenging activity/antioxidative effect (Kondo K., et al., Mechanistic studies of catechins as antioxidants against radical oxidation. Arch Biochem Biophys 1999 362:79-86), anti-cavity action, odor eliminating action, cholesterol lowering effects, blood sugar surge suppression effects, blood pressure surge suppression effects, anti-allergy effects, and platelet aggregation inhibition action. However, catechin's effect on biofilm formation was not known before the present invention.

The inventors of the present invention focused attention to catechins' bactericidal action which damages the cell membrane of all bacteria including *E. coli*, and gained a new understanding that catechins have effects on inhibiting biofilm formation. Based on this understanding, through serious examination and repeated experiments they have achieved the present invention. In other words, according to the biofilm formation inhibitor of the present invention, biofilm formation on a target medical device can be effectively inhibited by extermination and growth suppression of all bacteria including *E. Coli*.

Also, since catechins used in the biofilm formation inhibitor of the present invention are excreted via the duodenum, small intestine, and large intestine to the outside, it is believed that the risk to the living body for a long-term administration is small, compared to the above-mentioned drugs that have been used in the prior art. Especially, as for epigallocatechin gallate which effects were demonstrated in one of the examples of the present invention, no side effect has been reported, and a recent study has proved the safety of epigallocatechin gallate to the human body for a high dosage long-term oral administration. Thus, according to such configuration, biofilm formation is completely inhibited by exterminating or suppressing the growth of bacteria adhered to the surfaces of various medical devices such as biliary stent, thus offering safe and effective treatment materials for the human body.

Moreover, according to one embodiment of the present invention, in order to inhibit biofilm formation effectively, it is preferable that the above-mentioned catechin is contained in said carrier in an amount such that a sustained release of catechin per day is at least 0.22 mg/cm$^2$. Moreover, by modifying the content of a catechin in a carrier a sustained release amount can be controlled. Thus this sustained release amount can be selected depending on the mode used for the above-mentioned treatment materials and various factors of the application targets.

Furthermore, according to another embodiment of the present invention, the carrier is a hydrophilic biodegradable polymer. The hydrophilic biodegradable polymer has a high water content rate, and is subjected to hydrolytic degradation right away, thus facilitating catechin's sustained release and surface erosion. Furthermore, since the hydrophilic biodegradable polymer is liquid and easily photocurable by the irradiation of ultraviolet light, it is easily coated to the surface of a treatment substrate.

Furthermore, according to the second aspect of the present invention, there is provided a treatment device to be placed in a living body, wherein an effective amount of a catechin for inhibiting biofilm formation is coated on the surface thereon. According to such configuration, it becomes possible to manufacture a treatment device capable of inhibiting biofilm formation, by exterminating all bacteria including *E. coli* and by suppressing their growth.

According to one embodiment of the present invention, the treatment device obtained as described above is a biliary stent (although it is not limited to this), and it becomes possible to improve and treat obstructive jaundice that accompanies an advancing pancreatic carcinoma/bile duct cancer.

Further characteristics and prominent effects of this invention become clear for a person skilled in the art from the following descriptions.

BRIEF DESCRIPTION OF DRAWINGS

FIG. 6 (*a*), EGCg's loaded levels:
FIG. 6 (*b*)).
FIG. 13 shows the analysis of (drug) sensitivity of *E. coli* to EGCg.

DETAILED DESCRIPTION OF THE PREFERRED EMBODIMENTS

As mentioned earlier, the present invention provides a biofilm formation inhibitor which inhibits biofilm formation on a target treatment device by exterminating bacteria including *E. Coli* and suppressing their growth and a treatment device using thereof.

Figure 1:
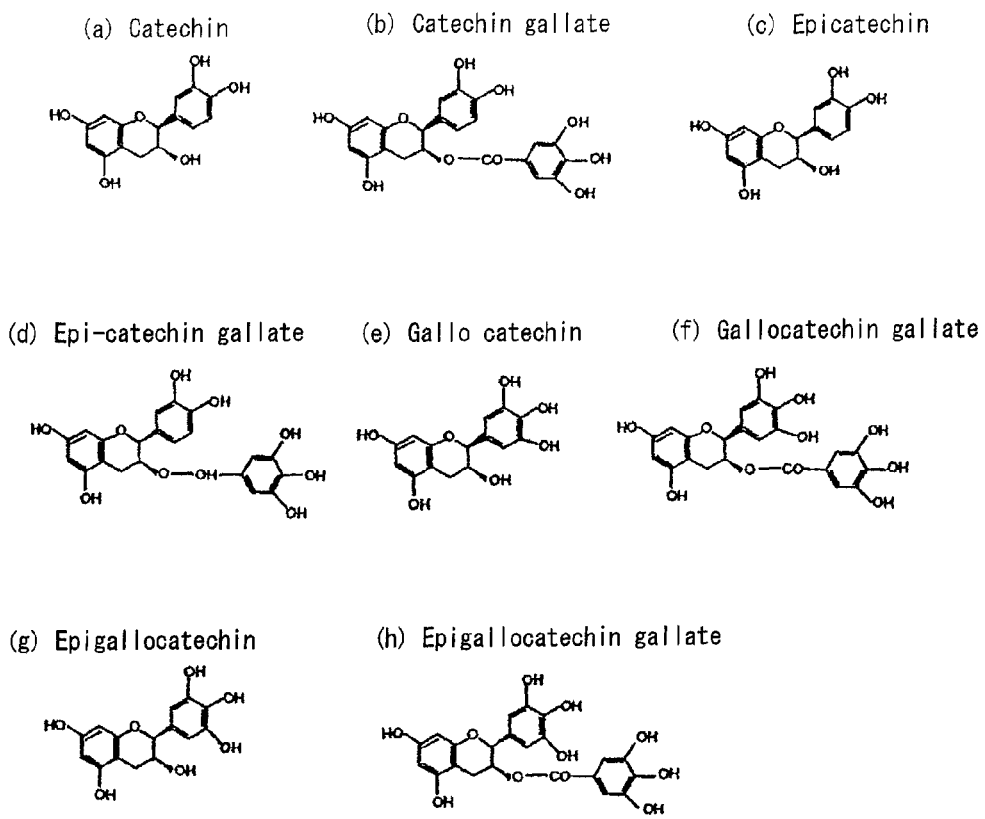
FIG. 1 shows the structure formulas of catechins.
Figure 2:
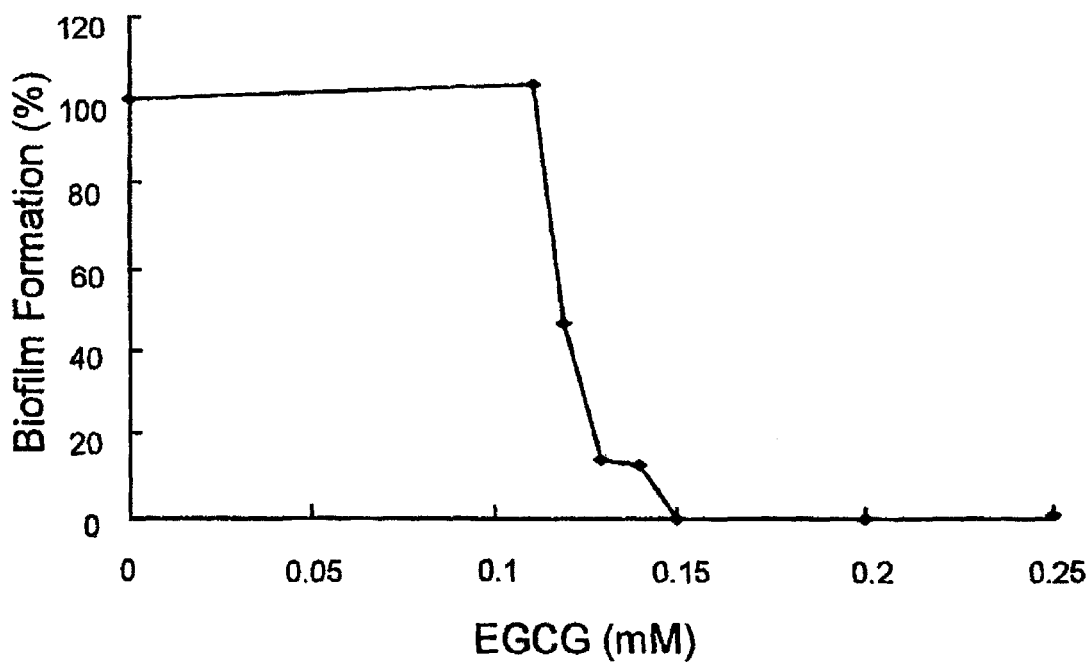
FIG. 2 shows the inhibitory effect of EGCg on biofilm formation.

Although not limited to the following, the catechins of the present invention include catechin, epicatechin, gallo catechin, epigallocatechin, catechin gallate, epi-catechin gallate, gallocatechin gallate, epigallocatechin gallate, etc. (which are shown by Formulas (a)-(h) in FIG. 1), and among them, epigallocatechin gallate (EGCg) is especially preferable, which has the strongest antibacterial action, that is, it has the smallest minimal inhibitory concentration against *E. coli*.

The above-mentioned catechins are included in a carrier suitable for coating on target treatment devices. For such a carrier, there is no special limitation as long as it is a biodegradable or non-biodegradable material which can be applied as a solvent and form a film by evaporation, and does not show toxicity. For example, polylactide, poly(2-hydroxy ethyl methacrylate) and polyethyleneglycol copolymer that form hydrophilic gel, and as hydrophobic materials, polyethylene terephthalate, polylactide, and acetylcellulose are preferable. Among them, hydrophilic biodegradable polymers are most preferable because the rate of their water content is high, and thus they are subjected to hydrolytic degradation immediately, facilitating the sustained release of catechins and surface erosion. When hydrophilic polymer or oligomer is soluble in water, the irradiation of ultraviolet light result in photocrosslinking, producing water-swellable polymers, thus they can facilitate the coating on the surface of a treatment material according to the present invention.

The manufacturing method of biofilm formation inhibitor of the present invention is not limited to a specific method, and it can be performed using a known art. For example, according to one example of the present invention, it can be manufactured by mixing epigallocatechin gallate which has been dissolved in acetone with a liquid-state biodegradable polymer.

As for the way to apply a biofilm formation inhibitor of the present invention, there is no particular limitation as long as it is for inhibiting biofilm formation by catechins. According to one example of the present invention, it can be applied to biliary stents to improve obstructive jaundice that accompanies an advancing pancreatic carcinoma/bile duct cancer. In other words, when using a biliary stent coated with a catechin-loaded polymer, that is one of the above-mentioned treatment materials, bacteria adhered on the surface of the biliary stent are exterminated, and thus biofilm formation is completely inhibited, making it possible to develop a biliary stent that can be placed in the living body for a long period of time. However, its target application is not limited to biliary stents, but can be used for other various treatment devices. For example, it can be used for a urethral catheter, a drainage tube for surgical operation, a central venous catheter, and a mesh for hemioplasty.

Moreover, the catechins used in the present invention are known to have various effects beside the above-mentioned antibacterial action. Thus, in addition to the inhibition of biofilm formation, the above mentioned treatment material can be used for growth suppression (antitumor effect by catechins) of malignant tumors (pancreatic carcinoma, bile duct cancer, etc.) that are in contact with the outer surface of a biliary stent; and for the suppression of gallstone formation in the biliary stent lumen (reactive oxygen scavenging action by the catechin).

Also, a treatment device of the present invention is provided by coating a biofilm formation inhibitor of the present invention to the above-mentioned target devices. The manufacturing method of such treatment device is not limited to a particular method, and can be manufactured using a publicly known technology. For example, when a treatment device is a biliary stent, a tube-shaped plastic material (polyurethane) which forms the substrate of the stent is soaked in a catechin loaded liquid polymer, and after being coated on its surface therewith, it is irradiated with UV ray to be hardened. While being hardened (approx. 5 min.), in order to avoid deviations in the thickness of the coating, the substrate is rotated around the axis of the stent lumen, thereby obtaining a biliary stent in which the above-mentioned biofilm inhibitor is coated inside.

Note that as for stent substrate, a substrate made of metal can also be used in addition to the above-mentioned substrate made of plastic, and the above-mentioned biofilm formation inhibitor may be applied to the metal stent substrate as well. However, a metal stent is a mesh-shaped self-expandable stent, and an occlusion is caused mainly by the aberrations of tumors. Thus, the biofilm is often not a cause of the occlusion. Therefore, a catechin-loaded surface-erodible polymer according to the present invention is considered effective mainly as a coating agent for a plastic stent with a narrow interior diameter.

In the examples explained next, among the polymers in which biofilm formation is significantly suppressed, the one with least amount of sustained releasing of catechin is the one in which 20 wt % of epigallocatechin gallate (EGCg) is incorporated in a biodegradable polymer (TMC/PEG200). Since the sustained release amount of catechin in the first 24 hours was 0.22 mg/cm$^2$, it is preferable that the above-mentioned catechin is included in a carrier in an amount such that the sustained release amount of catechin would be at least 0.22 mg/cm$^2$ per day. Moreover, by changing a carrier and the content of catechin in a carrier, the amount of sustained release can be controlled. Thus this amount of sustained release can be selected according to the embodiments in which the above-mentioned treatment materials are used and various factors of the application targets.

Next, the effect of the present invention is explained using examples. However, the present invention is not limited to the embodiments described below.

Example 1

The Inhibitory Effect of Epigallocatechin Gallate (EGCg) on Biofilm Formation 8 mm diameter disc shaped polyurethanes were cultured with an *E. coli* suspension ($2\times10^3$ CFU/ml) which was mixed with various concentrations of epigallocatechin gallate (EGCg) (0-0.2 mM) under a static condition at 37 degrees Celsius for 24 hours in a culture plate. After incubations, the polyurethane discs were taken out, and having been washed in a phosphate buffer gently, they were moved to a 2 ml phosphate buffer, where they were sonicated to detach the adhered *E. coli*. Viable *E. coli* cell counts in the liquid were calculated by the plate count method.

Figure 3:
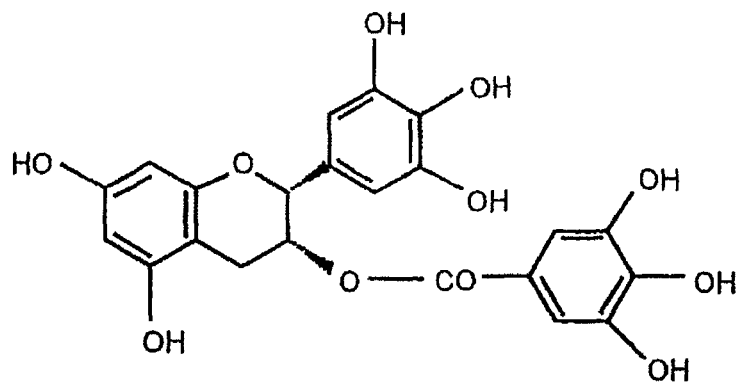
FIG. 3 shows the structure formula of epigallocatechin gallate (EGCg).
Figure 4:
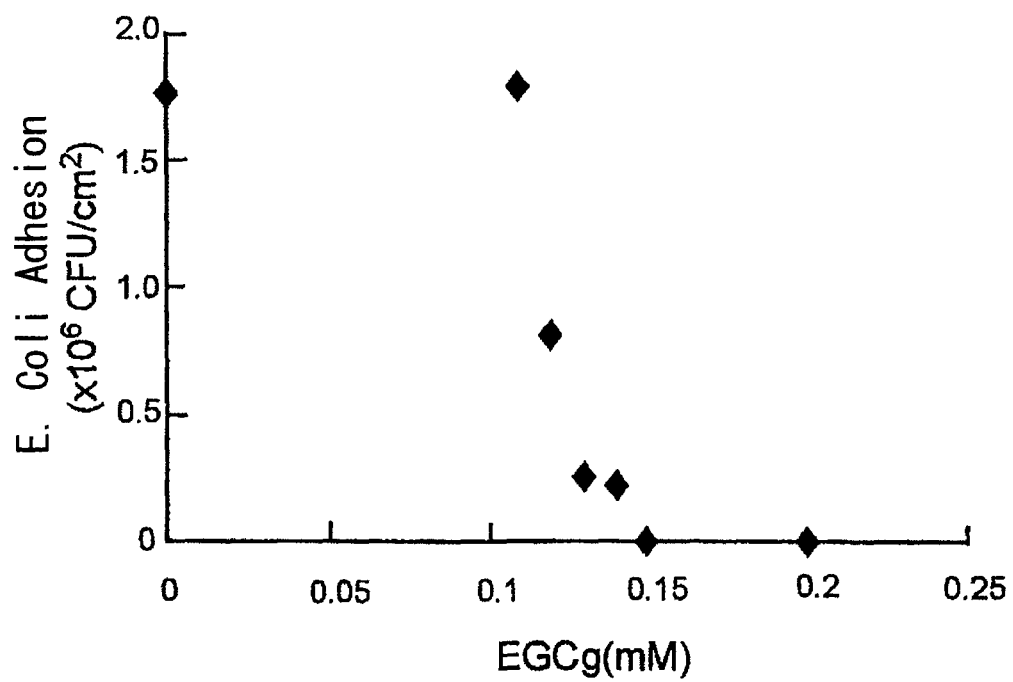
FIG. 4 shows the inhibitory effect of EGCg on the adhesion of *E. coli*.

As shown in FIG. 3 and FIG. 4, epigallocatechin gallate (EGCg) was proved to inhibit biofilm formation significantly at the concentration of 0.12 mM (0.055 mg/ml) and more, and to inhibit completely at the concentration of 0.15 mM (0.069 mg/ml) and more.

Example 2

Measurement of Sustained Release Amount of Catechin from Catechin-Loaded Polymer Epigallocatechin gallate (EGCg, Sigma—Aldrich, Inc., St. Louis, Mo.: shown in FIG. 3) dissolved in acetone (Sigma—Aldrich) was mixed with three kinds of biodegradable polymers (TMC/LL/PEG1k, TMC/PEG200, TMC/TMP: shown in FIG. 5 (*a*)-(*c*)) to make 20 wt % (wt %: weight percent). After acetone was volatilized in a low pressure tank over 24 hours, 250 mg of polymer was coated at the bottom (surface area 1.1 cm$^2$) of a glass bottle, and it was photocured by irradiating with ultraviolet light (SP-V, Ushio, Inc., Yokohama, Japan) for five minutes. 1 ml of phosphate buffer solution (Nissui Pharmaceutical Co., Ltd., Tokyo, Japan) was poured into the glass bottle and stoppered tightly, and kept at 37 degrees Celsius under static conditions for sustained release of EGCg. 100 μl of the solution in the glass bottle was taken out after one, two, and four days, and EGCg levels were calculated by the Folin-Ciocalteu method. As for TMC/LL/PEG1k, similar experiments were performed with EGCg concentrations of 5 and 10 wt %.

Figure 6A:
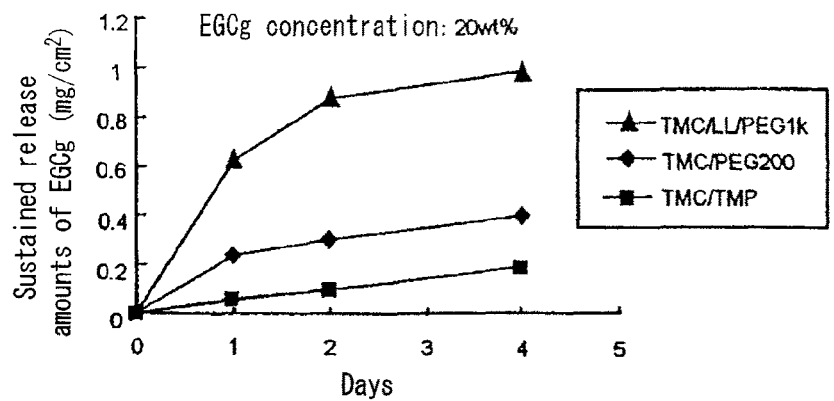
FIG. 6 shows sustained release amounts of catechin from the catechin-loaded polymers used in the present invention (polymer types.
Figure 6B:
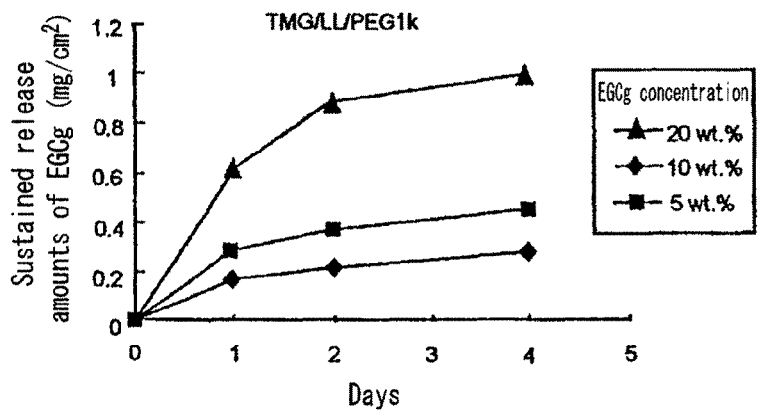

The results were shown in FIGS. 6 (*a*) and (*b*) with sustainedly released EGCg weight (mg/cm$^2$) per polymer surface area. FIG. 6 (*a*) shows that weights of EGCg increased in all polymer samples with time, and that EGCg was released over the period of 4 days. Compared among the polymers, LL/TMC/PEG1k which has the highest hydrophilic (wettability toward water) property and biodegradability had the highest sustained release amount and TMC/PEG200 was the second and then TMC/TMP, in that order. Also, as shown in FIG. 6 (*b*), with TMC/LL/PEG1k in which different degrees of EGCg were loaded, it was recognized that the higher the loading of EGCg the higher the amount of sustained release.

Example 3

The Inhibitory Effect of Catechin-Loaded Polymer on the Formation of Biofilm by *E. coli*(Static Conditions)

Figure 5:
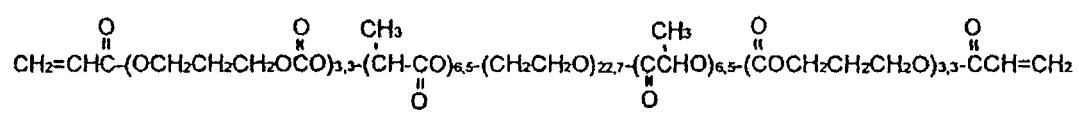
FIG. 5 shows structure formulas of biodegradable liquid polymers (TMC/LL/PEG1k, TMC/PEG200, TMC/TMP) used in the present invention.
Figure 5:
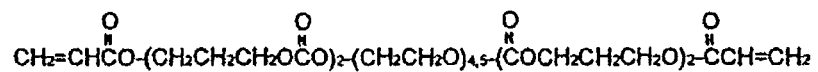
Figure 5:
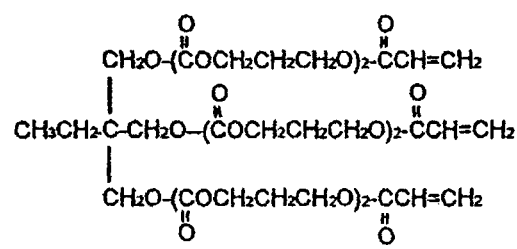

EGCg dissolved in acetone was mixed with three kinds of liquid biodegradable polymers (TMC/LL/PEG1k, TMC/PEG200, and TMC/TMP: shown in the FIG. 5 (a)-(c)) to make 0, 5, 10, and 20 wt % (wt %: weight percent). These polymers were spin-coated on polyurethane surfaces, and after having been irradiated with UV for five minutes, and solidified, and 8 mm diameter disc samples were punched out by a belt punch. These samples were incubated at 37 degrees Celsius with an *E. coli* suspension ($2 \times 10^3$ CFU/ml) in a culture plate for 24 hours. After incubation, the samples were taken out and washed in a phosphate buffer gently, and then they were moved to 2 ml of phosphate buffer solution where they are sonicated to detach the adhered *E. coli*. Viable *E. coli* cell count in this liquid was calculated by the plate count method.

Figure 7:
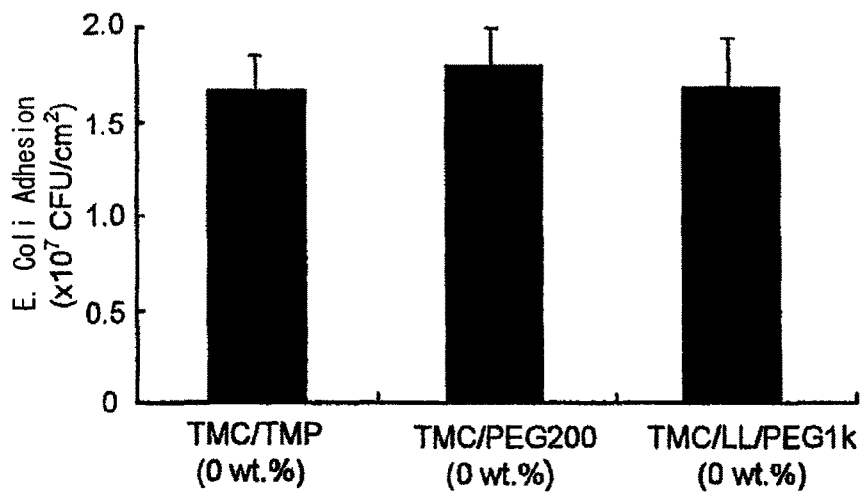
FIG. 7 shows the effect of non-EGCg loaded polymers (TMC/LL/PEG1k, TMC/PEG200, TMC/TMP) on the adhesion of *E. coli* under static conditions.
Figure 8A:
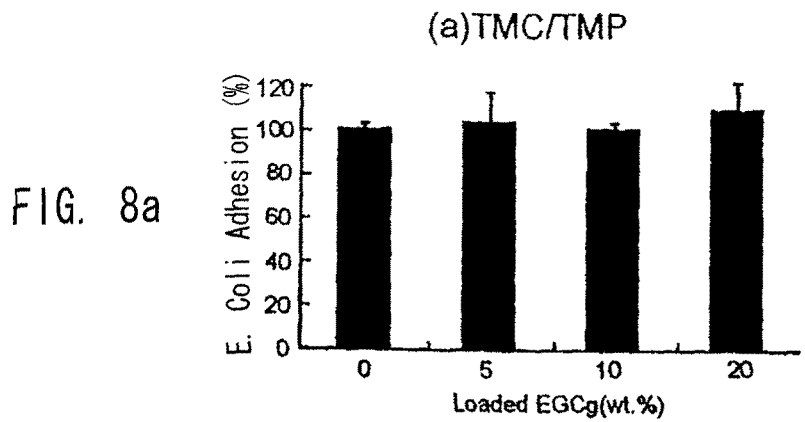
FIG. 8 shows the effect of EGCg-loaded biodegradable polymers (TMC/LL/PEG1k, TMC/PEG200, and TMC/TMP) on the adhesion of *E. coli* of EGCg loaded (0, 5, 10, and 20 wt %, wt %: weight percent) under static conditions.
Figure 8B:
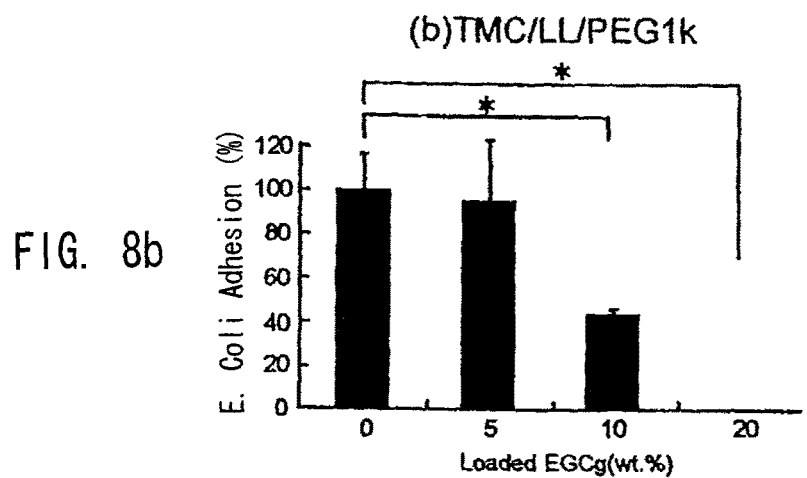
Figure 8C:
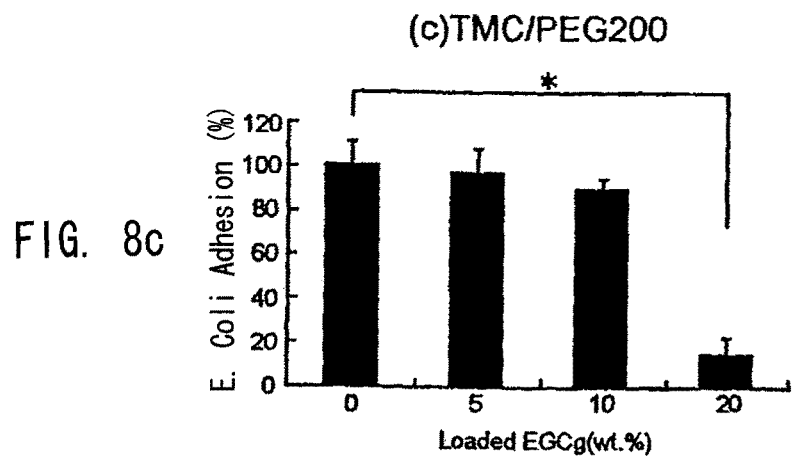

These results were shown in FIG. 7 and FIG. 8. According to FIG. 7, concerning the adhesion of *E. coli*, no significant difference was recognized among the non-EGCg loaded polymers of TMC/LL/PEG1k, TMC/PEG200, and TMC/TMP. According to FIGS. 8, 10 and 20 wt % EGCg loaded TMC/LL/PEG1k and 20 wt % EGCg loaded TMC/PEG200 inhibited *E. coli* adhesion significantly as compared with the polymers having no EGCg (0 wt %). In particular, with the 20 wt % EGCg loaded TMC/LL/PEG1k, *E. coli* adhesion was completely obstructed. These results are proportional to the catechin release amounts in Example 2. Thus it is suggested that the adhesion of *E. coli* is obstructed according to the amount of catechin release. Note that an *E. coli* adhesion (%) was converted with the value being 100% for the 0 wt % loaded EGCg concentration for the respective polymers.

Figure 9:
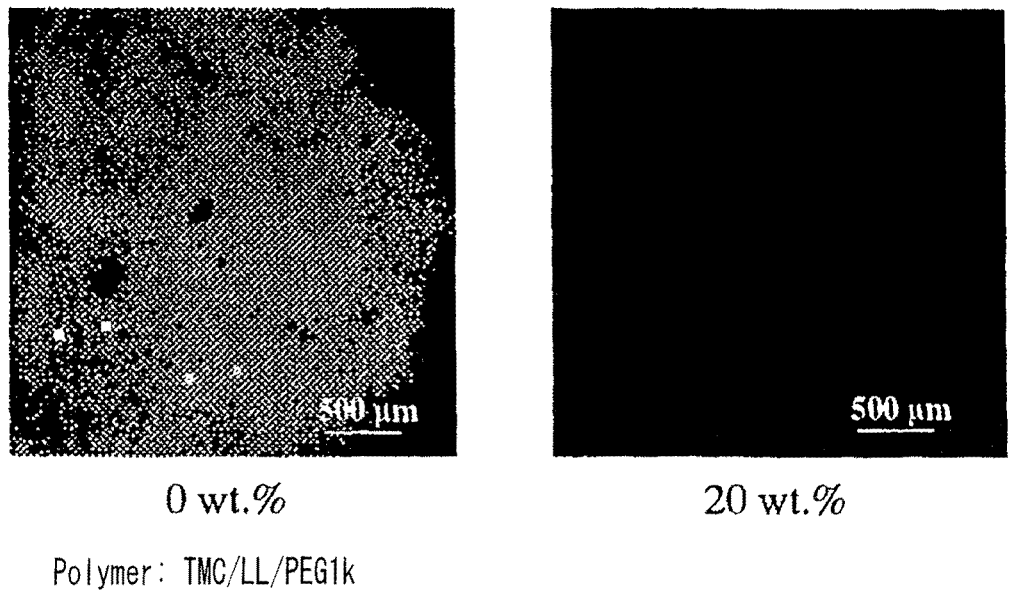
FIG. 9 shows the condition of biofilm formation on catechin-loaded polymers))) EGCg/(TMC/LL/PEG1k) surface using confocal laser microphotographs.

Furthermore, biofilm formation on the surface of the catechin-loaded polymer EGCG/(TMC/LL/PEG1k) was observed with a confocal laser microscope. As explained above, disk shaped polyurethanes (8 mm diameter), on which 0 and 20 wt % EGCg loaded TMC/LL/PEG1k was coated, were incubated with a suspension of *E. coli* which was transformed to express green fluorescence protein ($2 \times 10^3$ CFU/ml) at 37 degrees Celsius for 24 hours under a static condition. After having washed the polymer surfaces on which biofilms were formed with a phosphate buffer gently, they were observed with a confocal laser microscope (Radiance2000, BioRed, Hercules, Calif.). As shown in FIG. 9, while *E. coli* which expressed GFR grew and formed biofilms on the polymer surfaces in no EGCg loaded TMC/LL/PEG1k (0 wt %), no biofilm formation was recognized on the 20 wt % EGCg loaded TMC/LL/PEG1k. The biofilm inhibiting effect of catechin-loaded polymers was proven from image findings as well.

Example 4

The Inhibitory Effect of Catechin-Loaded Polymer on Biofilm Formation by *E. coli* (Dynamic Condition)

Figure 10:
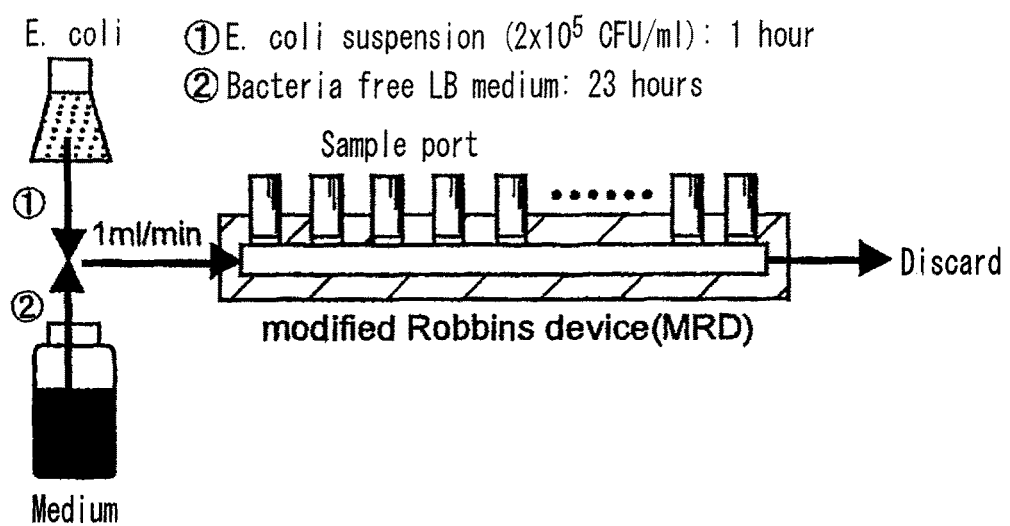
FIG. 10 shows a Modified Robbins device and an experimental procedure.

This experiment used a Modified Robbins device (Tyler Co., Edmonton, Canada) shown in FIG. 10. Samples with 8 mm diameter that were made similarly to the one in Example 3 were glued to a sample port using a silicon glue. After passing *E. coli* suspension ($2 \times 10^5$ CFU/ml) through the flow path at 1 ml/min for one hour, followed by the passing of the bacteria free LB medium for 23 hours, *E. coli* adhesion was determined by a method similar to Example 2.

Figure 11:
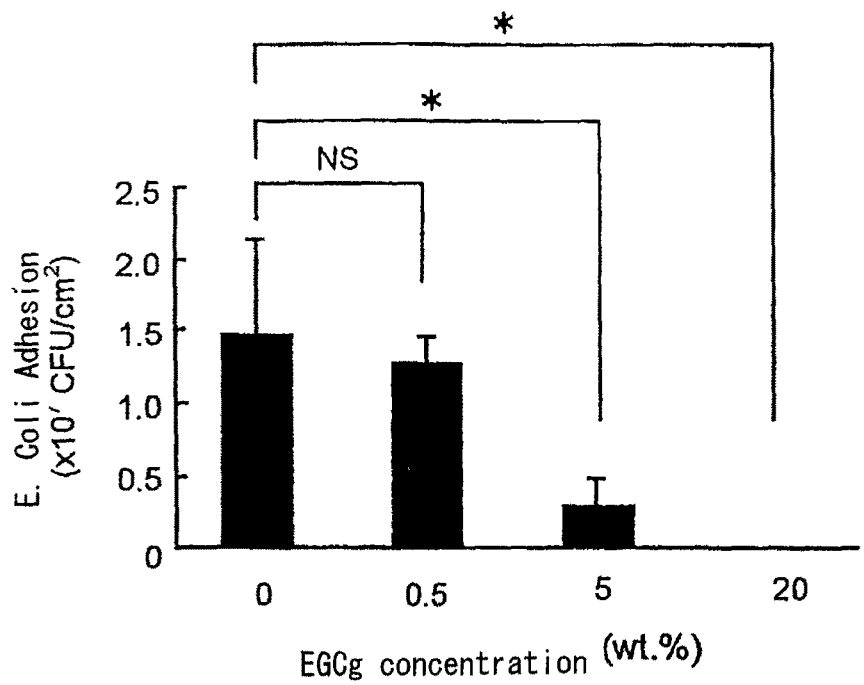
FIG. 11 shows the effect of catechin-loaded polymers EGCg/(TMC/LL/PEG1k) on the adhesion of *E. coli* under dynamic conditions.

As results, 5 and 20 wt % EGCg loaded TMC/LL/PEG1k showed significant inhibition of *E. coli* adhesion as compared to the no EGCg loaded polymer (0 wt %) (FIG. 11). Because adhesion was not inhibited in the 5 wt % EGCg loaded TMC/LL/PEG1k under the static condition of Example 2, it is suggested that under a dynamic condition, biofilm formation is inhibited with a smaller concentration of EGCg in the polymer.

Example 5

The Effect of EGCg on Living Microbes after Biofilm Formation

Figure 12:
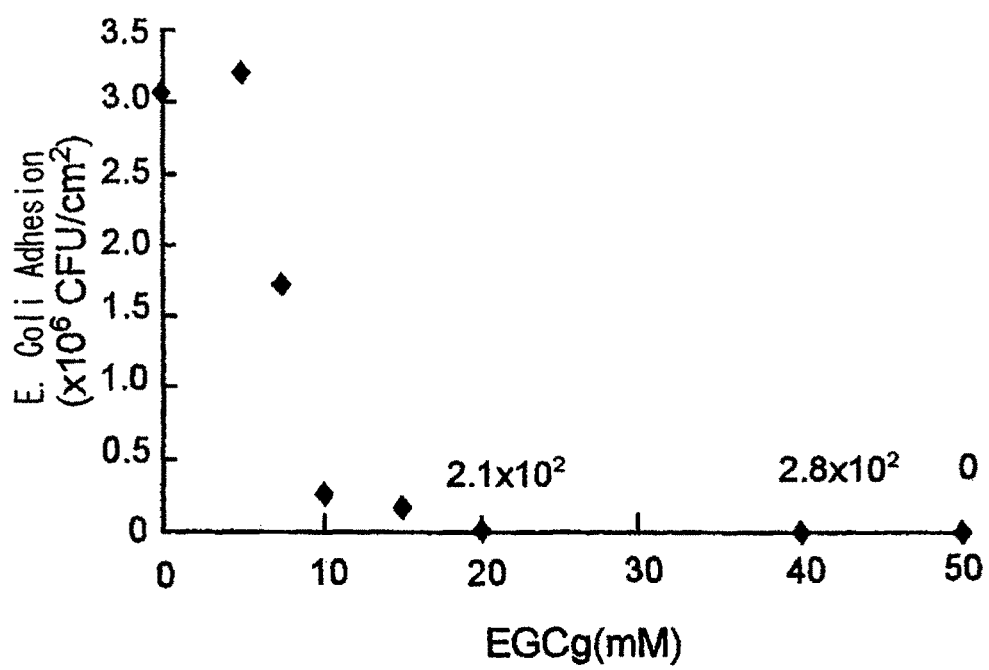
FIG. 12 shows the effect of EGCg on living microbes within biofilm after formation of the biofilm.

Biofilms were formed on polyurethane surfaces after incubating 8 mm diameter polyurethane discs placed in a culture plate with an *E. coli* suspension ($2 \times 10^3$ CFU/ml) under a static condition at 37 degrees Celsius for 24 hours. After adding solutions with various degrees of epigallocatechin gallate (EGCg) concentration (0-50 mM) to the biofilm surfaces that were formed, they were exposed for another 24 hours. After the polyurethane discs were taken out, and washed with a phosphate buffer solution gently, they were moved to a 2 ml phosphate buffer solution and sonicated to detach adhered *E. coli*. Viable *E. coli* cell count in this liquid was counted by the plate count method. As shown in the graph of FIG. 12, it was proved that, when the concentration of epigallocatechin gallate (EGCg) was 8 mM (3.7 mg/ml) and more, viable cell counts decreased significantly, and at 50 mM (23 mg/ml) *E. coli* in biofilm were exterminated completely. These levels of concentration are much higher compared to the Example 1 where catechin was placed from the beginning of incubation. Thus this shows that once a biofilm is formed, *E. coli* therein shows resistance to catechin.

Example 6

The Analysis of the Sensitivity of *E. coli* to EGCg

Sensitivity of *E. coli* to EGCg was examined by a general sensibility test method (dilution method). *E. coli* suspensions ($1 \times 10^7$ CFU/ml), in which gradually diluted (0.16, 0.31, 0.63, 1.25, 2.5, 5.0 mM) epigallocatechin gallate (EGCg) solutions were mixed, were placed in a culture plate and incubated at 37 degrees Celsius for 24 hours under a static condition. Minimal inhibitory concentration (MIC) was defined as the smallest EGCg concentration in which no bacteria growth is recognized macroscopically. As shown in FIG. 13, the minimal inhibitory concentration (MIC) was 0.63 mM (287 µg/ml).

From the results of FIG. 7 and FIG. 8, among the polymers in which biofilm formation is significantly suppressed, the one with the least amount of sustained releasing of catechin is the one in which 20 wt % of epigallocatechin gallate (EGCg) was incorporated in TMC/PEG200. Furthermore, since the sustained release amount of catechin from this polymer is 0.22 mg/cm$^2$ in the initial 24 hours, it is suggested that the catechin is preferably included in a carrier in an amount such that the sustained release of catechin per day is at least 0.22 mg/cm$^2$.

What is claimed is:

1. A biofilm formation inhibitor comprising an effective amount of an isolated catechin for inhibiting biofilm formation by *E. Coli* and a hydrophilic biodegradable polymer that is suitable for adhesion of said catechin to a biliary stent to be placed in a living body and that is capable of sustained releasing of said isolated catechin and surface erosion.

2. The biofilm formation inhibitor of claim 1, wherein said catechin is epigallocatechin gallate.

3. The biofilm formation inhibitor of claim 1, wherein said catechin is contained in said carrier in an amount such that a sustained release of said catechin per day is at least 0.22 mg/cm$^2$.

4. A biliary stent to be placed in a living body, wherein an effective amount of an isolated catechin for inhibiting biofilm formation by *E. Coli* is coated on the surface thereon with a hydrophilic biodegradable polymer, and which allows sustained releasing of said catechin and surface erosion.

5. The biliary stent of claim 4, wherein said biliary stent is a plastic stent of a non-self-expandable type.

6. The biliary stent of claim 4, wherein said catechin is coated thereon as contained in a carrier in an amount such that a sustained release of said catechin per day is at least 0.22 mg/cm$^2$.

7. The biofilm formation inhibitor of claim 1, wherein said hydrophilic biodegradable polymer is selected from the group consisting of TMC/LL/PEG1k, TMC/PEG200, and TMC/TMP.

8. The biliary stent of claim 4, wherein said hydrophilic biodegradable polymer selected from the group consisting of TMC/LL/PEG1k, TMC/PEG200, and TMC/TMP.

9. The biofilm formation inhibitor of claim 1, wherein said isolated catechin is selected from the group consisting of catechin, epicatechin, gallo catechin, epigallocatechin, catechin gallate, epi-catechin gallate, gallocatechin gallate, and epigallocatechin gallate.

10. The biliary stent of claim 4, wherein said isolated catechin is selected from the group consisting of catechin, epicatechin, gallo catechin, epigallocatechin, catechin gallate, epi-catechin gallate, gallocatechin gallate, and epigallocatechin gallate.

* * * * *

UNITED STATES PATENT AND TRADEMARK OFFICE
CERTIFICATE OF CORRECTION

PATENT NO. : 8,540,766 B2  Page 1 of 1
APPLICATION NO. : 11/719819
DATED : September 24, 2013
INVENTOR(S) : Matsuda et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 899 days.

Signed and Sealed this
Fifteenth Day of September, 2015

Michelle K. Lee
*Director of the United States Patent and Trademark Office*